United States Patent
Forrester

(10) Patent No.: US 11,660,358 B1
(45) Date of Patent: May 30, 2023

(54) HAND-HELD GAS POWERED STEAMER FOR APPLYING SCENT REDUCING AND COVER SCENT PREPARATIONS TO APPAREL AND GEAR IN THE FIELD

(71) Applicant: Darrell Forrester, Farmington, KY (US)

(72) Inventor: Darrell Forrester, Farmington, KY (US)

( * ) Notice: Subject to any disclaimer, the term of this patent is extended or adjusted under 35 U.S.C. 154(b) by 0 days.

(21) Appl. No.: 16/134,710

(22) Filed: Sep. 18, 2018

Related U.S. Application Data

(60) Provisional application No. 62/560,052, filed on Sep. 18, 2017, provisional application No. 62/567,853, filed on Oct. 4, 2017.

(51) Int. Cl.
| | |
|---|---|
| *A61L 2/07* | (2006.01) |
| *D06B 19/00* | (2006.01) |
| *D06B 21/00* | (2006.01) |
| *A01M 31/00* | (2006.01) |
| *F22B 1/18* | (2006.01) |
| *D06F 39/00* | (2020.01) |
| *A41D 1/02* | (2006.01) |

(52) U.S. Cl.
CPC .............. *A61L 2/07* (2013.01); *A01M 31/00* (2013.01); *D06B 19/0029* (2013.01); *D06B 21/00* (2013.01); *D06F 39/008* (2013.01); *F22B 1/18* (2013.01); *A41D 1/02* (2013.01); *A61L 2202/26* (2013.01); *D10B 2507/00* (2013.01)

(58) Field of Classification Search
CPC ....................................................... A61L 2/07
See application file for complete search history.

(56) References Cited

U.S. PATENT DOCUMENTS

| | | | | |
|---|---|---|---|---|
| 3,745,306 A | * | 7/1973 | Naritomi ............... | A45D 19/16 392/335 |
| 2011/0236275 A1 | * | 9/2011 | Robertson et al. ....... | A61L 2/07 422/291 |
| 2013/0037063 A1 | * | 2/2013 | King ........................ | A61L 2/07 134/31 |
| 2016/0310624 A1 | * | 10/2016 | Wynalda, Jr. ........... | F22B 1/284 |
| 2018/0371684 A1 | * | 12/2018 | Ong et al. .............. | D06F 75/12 |

OTHER PUBLICATIONS

Dick's Pro Tips. Scent Control on the Hunt. Wayback Machine Capture from Apr. 18, 2017 (Year: 2017).*
US Department of Energy. "Energy Tips: STEAM". Apr. 2012. (Year: 2012).*

* cited by examiner

*Primary Examiner* — Donald R Spamer
(74) *Attorney, Agent, or Firm* — C. Brandon Browning; Maynard, Cooper & Gale, PC

(57) ABSTRACT

An apparatus and method for masking or reducing undesired scents emanating from hunting and military gear, the method including providing a hand-held, cordless steamer having a reservoir, a boiler, a gas combustion device and a gas cartridge, adding a liquid cover scent preparation or a liquid scent reducing preparation to the reservoir, pumping the cover scent preparation or the scent reducing preparation from the reservoir to the boiler, using the gas combustion device to ignite and combust a gas delivered from the source of gas thereby creating heat which is used to convert the liquid in the boiler into a steam, and applying the steam directly to a piece of hunting or military gear.

26 Claims, 5 Drawing Sheets

HAND-HELD GAS POWERED STEAMER FOR APPLYING SCENT REDUCING AND COVER SCENT PREPARATIONS TO APPAREL AND GEAR IN THE FIELD

RELATED APPLICATIONS

This application claims priority to U.S. Provisional Pat. Application No. 62/560,052 titled, "Method of Applying Scent Elimination Preparation to Hunting Apparel and Gear," filed Sep. 18, 2017, and U.S. Provisional Pat. Application No. 62/567,853 titled, "Method of Applying Scent Elimination Preparation to Military Apparel and Gear," filed Oct. 4, 2017, the entire contents of which are incorporated herein.

FIELD OF INVENTION

The present invention is directed to an apparatus and method for applying fluid preparations to apparel and gear and, more particularly, to a method of applying cover scent preparations and scent reducing preparations to hunting and military apparel and gear using a cordless, hand-held, gas-powered steamer.

BACKGROUND OF INVENTION

When hunting a game animal, e.g., deer, elk, bear, etc. having a keen sense of smell, the success of the hunt often relies on the ability of the hunter to prevent the animal from smelling the hunter. In many instances, the primary scent that is detected by a game animal originates from the clothing worn by the hunter or the hunter's hunting gear. The undesirable smells often arise from bacteria living on and within the clothing and gear or volatile chemicals within the gear.

A hunter can minimize the likelihood of being smelled or winded by an animal by approaching the animal from downwind of the animal or setting up downwind from the location where the animal is anticipated to be, such as a green field or around bait. However, in certain instances this strategy fails, either because the wind changes direction or a field or animal may not be approached or hunted from a downwind location.

Another strategy for preventing being winded by an animal is to address the source of the undesired available on the market intended for this purpose. Some preparations function to cover or mask such scents. Exemplary cover scents include animal urine preparations such as fox urine and raccoon urine, and plant-based preparations such as pine tree scents and cedar tree scents, including the cover scents CodeBlue coon urine cover scent and CodeBlue fox urine Cover Scent available from Ebsco Industries, Inc. located at 5724 Highway 280 East, Birmingham, AL 35242, Harmon cedar cover scent available from Altus Brands, LLC located at 6893 Sullivan Road, Grawn, MI 49637 and Buck Baits pine cover scent available from Buck Baits, LLC located at 13335 15 Mile Road, Suite 255, Sterling Heights, MI 48312. Other preparations function to reduce the undesired scents to level undetectable by game animals, the most problematic of which are human odors. Scent reducing preparations work by killing bacteria, binding to volatile chemicals in the clothing that cause undesired smells or converting the chemicals into less volatile compounds. Exemplary scent reducing preparations include Super Charged Scent Killer Autumn Formula hunters' scent camouflage and neutralizer and Super Charged Scent Killer Gold available from Wildlife Research Center, Inc. located at 14485 Azurite Street NW, Ramsey, MN 55303 and CodeBlue scent reducing field spray from Ebsco, Industries, Inc., all of which are designed to reduce human odors to levels that are undetectable by game animals.

The problem with undesired scents and scent detection is also experienced by soldiers in the field. Often, a soldier's scent is detected by an enemy force. This can arise from the soldier's gear coming into contact with odiferous materials. For example, this can arise from the soldier wearing the gear while smoking tobacco products, wearing the gear in the presence of food or the cooking of food, or contacting the gear with petroleum products such as fuel or motor oil.

Most scent reducing preparations are applied to clothing and gear by spraying the preparations directly onto the outer surfaces of the clothing and gear. A shortcoming of this application method is that the preparations do not come into contact with bacteria or chemicals causing the smell when the bacteria or chemicals are located within the clothing and spaced apart from the outer surfaces thereof. Other methods include washing hunting gear with unscented laundry detergent and applying cleaning/refreshment compositions to clothing using an ultrasonic nebulizer, for example as described in U.S. Pat. Application Publication No. 2002/0053607. The primary shortcoming of both methods is that they cannot be used in the field. Thus, they do not allow application or reapplication of desired compositions to clothing and gear while the clothing or gear are in use, which is needed in the event the clothing or gear contacts odiferous compositions while in transit to, or on location at, a hunting location or field of operation. This can occur, for example, when wearing hunting apparel while pumping gasoline, smoking a cigarette, coming into contact with a dog or the build-up of body odor and sweat within apparel during its use in the field. What is needed is an apparatus and method for applying scent reducing preparations to both the inner and outer surfaces of clothing and gear in the field.

BRIEF SUMMARY OF THE INVENTION

The present invention is directed to a method of reducing or masking undesired scents from hunting gear, military gear and tactical gear. According to one aspect of the invention, there is provided a method of masking or decreasing undesired smells emanating from hunting or military gear including providing a steamer including a boiler, a reservoir operatively coupled to the boiler, a gas combustion device and a source of gas, wherein the steamer is hand-held and cordless. A liquid is added to the reservoir which may be selected from a cover scent preparation and a scent reducing preparation. Suitable preparations include those described above available from Ebsco Industries, Inc., Altus Brands, LLC, Buck Baits, LLC and Wildlife Research Center, Inc. Cover scents are typically used to mask undesired scents, while scent reducing preparations are used to decrease the undesired scents to level undetectable by game animals. In use, the gas combustion device is used to ignite and combust a gas delivered from the source of gas thereby creating heat which is used to heat the boiler and convert liquid pumped into the boiler from the reservoir into a steam. The gas can be any suitable combustible gas such as butane gas or propane gas. The steam is then applied to a piece of hunting or military gear thereby masking or decreasing undesired smells emanating from the piece of hunting or military gear. Hunting and military gear suitable for treatment with the method include apparel, shirts, headwear, footwear, jackets, body armor, helmets, body suits, pants, face coverings, weapons, scarves, ear coverings, gloves, underwear, socks, binoculars, seat cushions, firearms, archery bows, hunting blinds, animal calls, hunting stands, range-finders, ammunition containers, weapon cases, motor-vehicles, motor-vehicle interior fabric, Ghillie suits, parachutes, backpacks, bags, sacks, weapon holsters, hydration packs and a rappelling kits.

When the hunting or military gear is porous, the steam penetrates the gear thereby contacting both outer surfaces and inner surfaces of the hunting or military gear. In certain instances, the liquid binds to scent-causing chemicals located on both the outer and inner surfaces of the hunting or military gear thereby neutralizing the chemicals, while the heat carried by the steam kills scent-causing organisms living on or within the gear. Contrary thereto, prior art methods for applying cover scent preparations and scent reducing preparations to hunting and military gear treat only the outer surfaces of the gear. As a consequence, undesired smells emanating from the interior surfaces of the gear are not treated, including, for example, undesired smells emanating from insulation located within apparel. For best results, the scent-reducing preparation-based steam is applied to the gear first, followed by application of the cover scent-based steam.

Another benefit of the present invention is the ability to apply cover scent preparations and scent reducing preparations to hunting or military gear in the form of steam while in the field. By "in the field," it is meant while the gear is located in or near the location where hunting or military operations are to take place and away from structures connected to the electrical grid or other sources of electrical power. For a hunter, this may include while the gear is being worn or carried by the hunter during a hunting excursion or while the hunter and gear are located in a hunting stand or blind stationed in a location were game is found. For a soldier, this may include while the soldier and gear are being transported to a site wear military operations are to take place or while the gear is being worn or carried by the soldier during a military operation.

According to another aspect of the invention is there is provided a system for masking or decreasing undesired smells emanating from hunting or military gear, the system including a cordless, hand-holdable body having a handle portion and a nozzle portion, a boiler, a reservoir for containing a liquid, such as a cover scent preparation or a scent reducing preparation, and a gas combustion device in a heat exchange relationship with the boiler, the gas combustion device being configured for igniting and burning as a gas supplied by a gas cartridge detachably coupled to a rear section of the nozzle portion. A pump is provided for pumping the liquid from the reservoir to the boiler, and a battery assembly is provided for selectively activating the pump and the gas combustion device. One or more switches are included for selectively activating the pump and selectively supplying the gas from the gas cartridge to the gas combustion device. The switches may include an ignition switch for igniting gas supplied to the gas combustion device, a gas switch for selectively supplying gas from the gas cartridge to the gas combustion device, and a pump switch for selectively activating the pump.

According to another aspect of the invention, there is provided a method of masking or decreasing undesired smells emanating from hunting or military gear including providing a steamer, adding a liquid to the steamer, the liquid being selected from the group consisting of a cover scent preparation and a scent reducing preparation, using the steamer to convert the liquid into a steam, and applying the steam to a piece of hunting or military gear thereby masking or decreasing undesired smells emanating from the piece of hunting or military gear. The steamer may be cordless and include a reservoir containing the liquid, a boiler operatively coupled to the reservoir, a gas combustion device arranged in a heat exchange relationship with the boiler and a gas cartridge operatively coupled to the gas combustion device.

BRIEF DESCRIPTION OF DRAWINGS

The disclosure can be better understood with reference to the following drawings. The elements of the drawings are not necessarily to scale relative to each other, emphasis instead being placed upon clearly illustrating the principles of the disclosure. Further, like reference numerals designate corresponding parts throughout the several views.

DETAILED DESCRIPTION OF THE INVENTION

Figure 1:
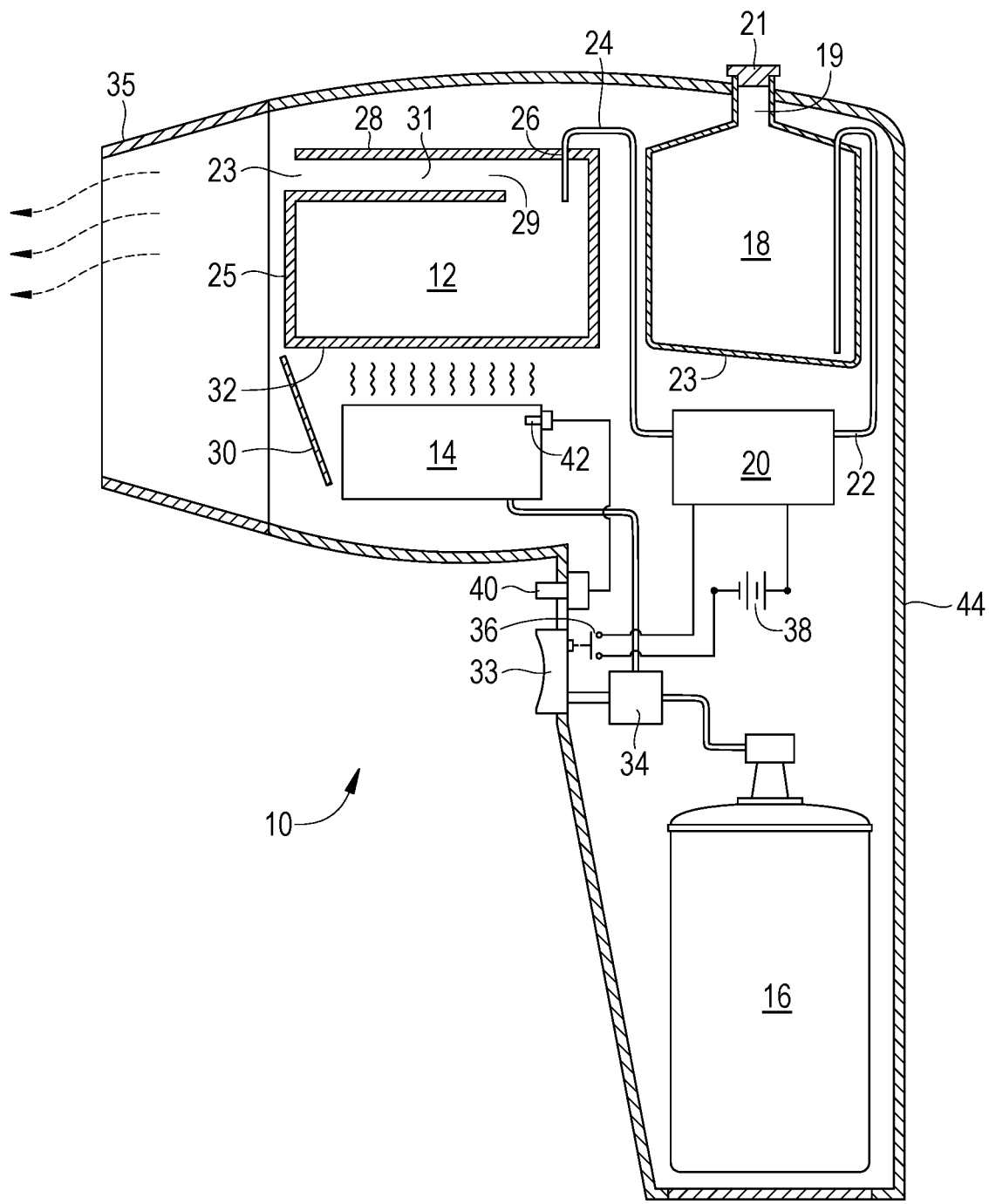
FIG. 1 is a sectional view of a steamer in accordance with the present invention.
Figure 2:
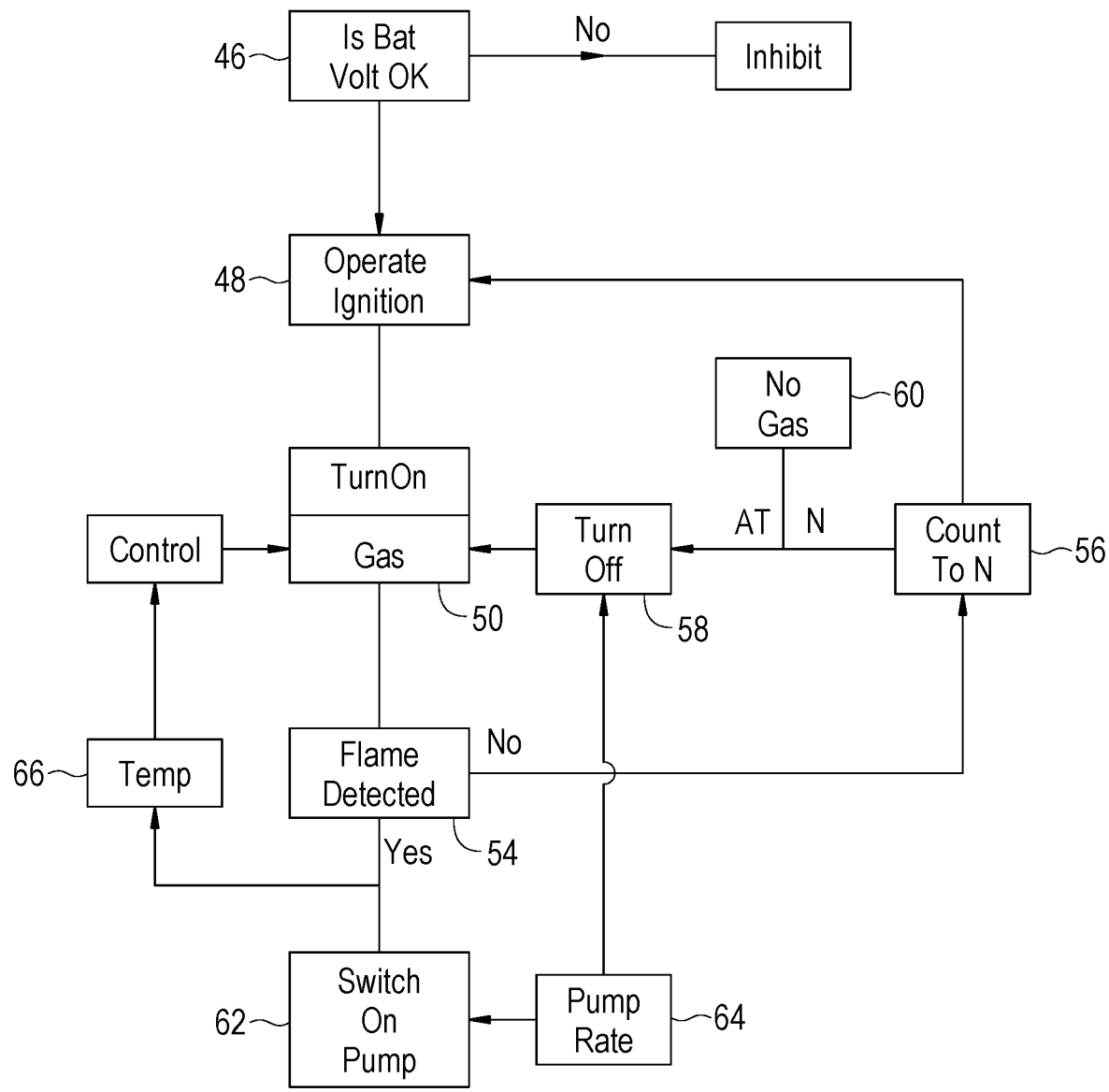
FIG. 2 is a control circuit diagram for the steamer of FIG. 1.
Figure 3:
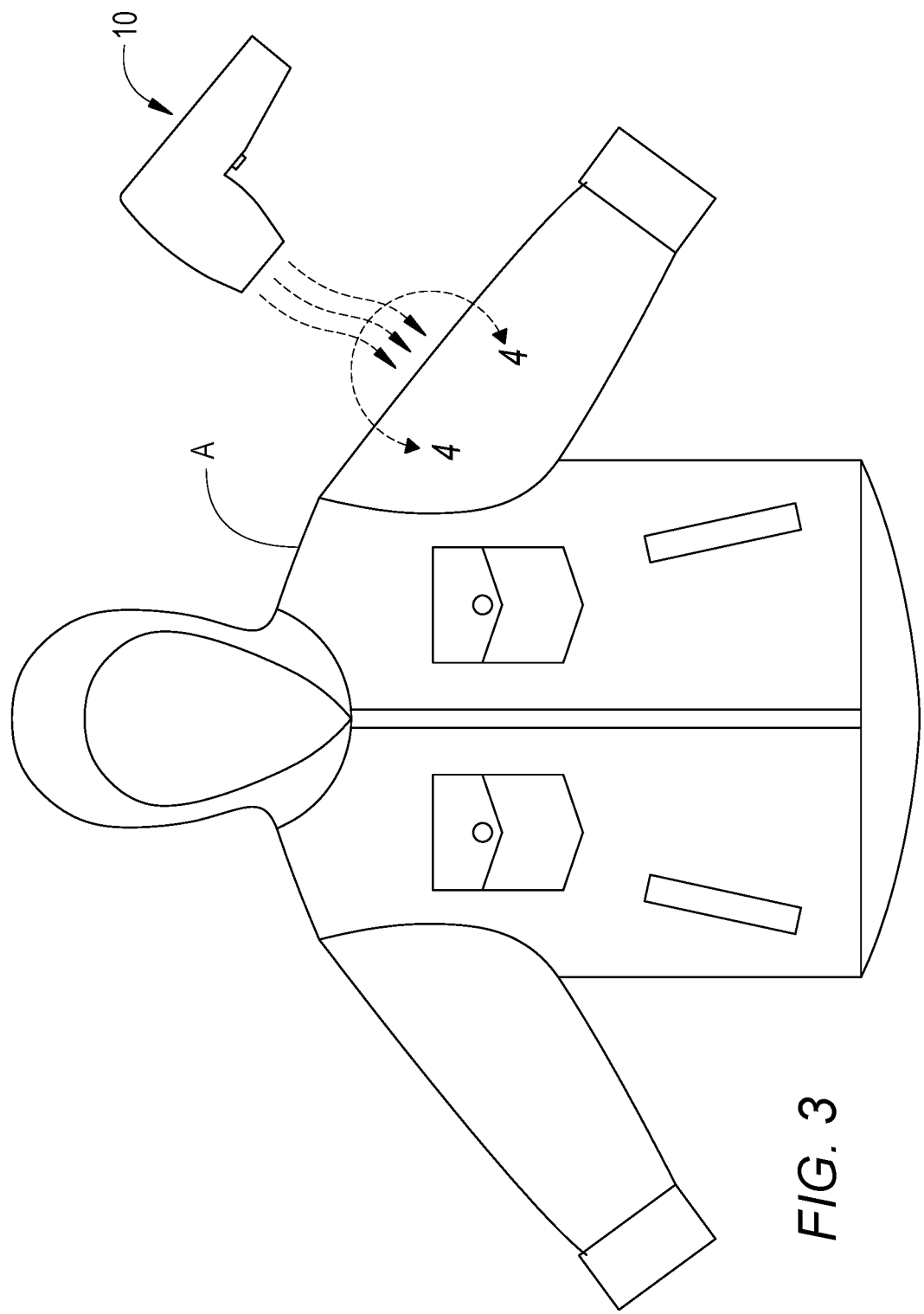
FIG. 3 is a perspective view of the steamer of FIG. 1 being used to treat a piece of clothing.
Figure 4:
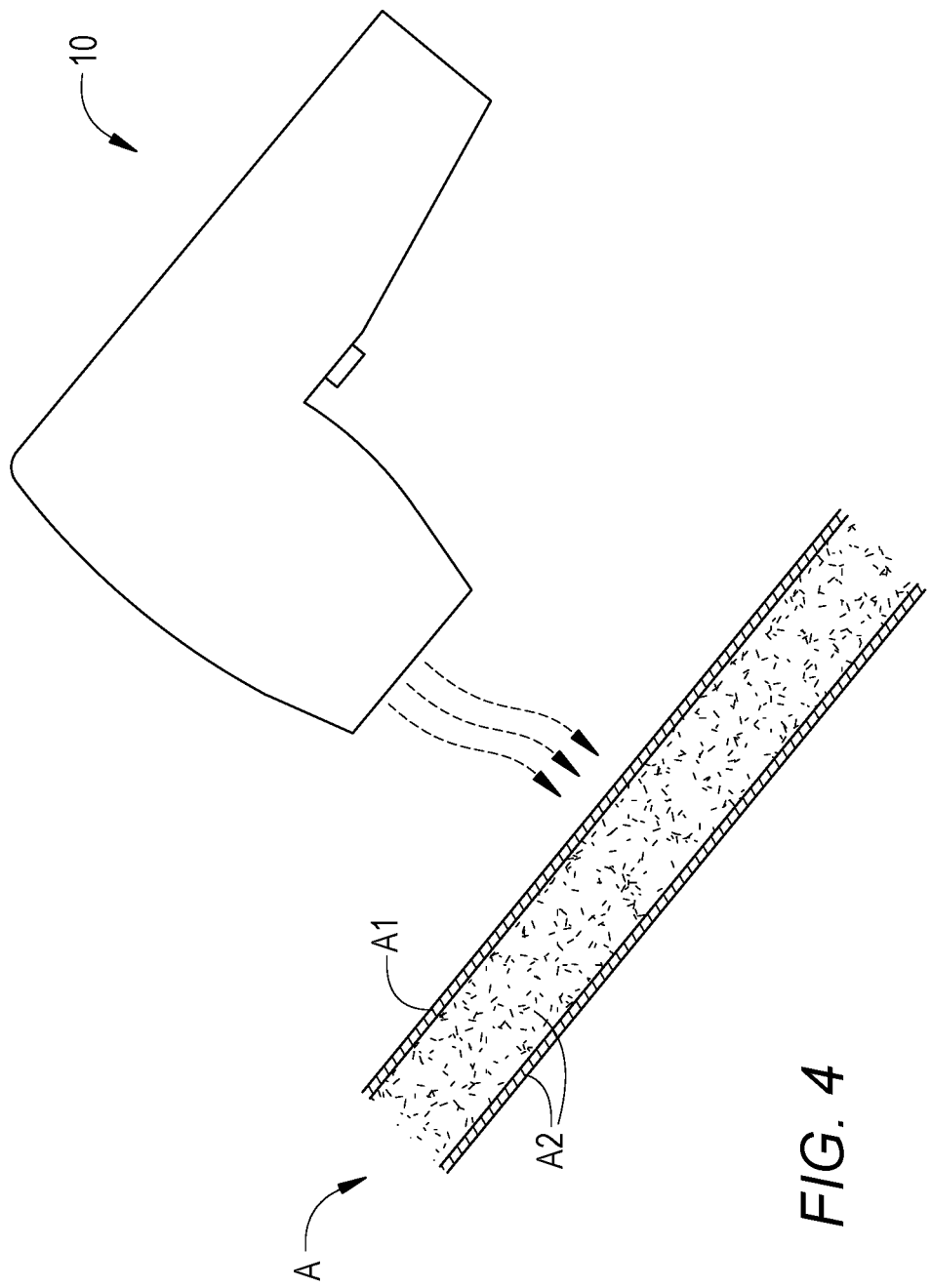
FIG. 4 is a close-up, sectional view of the piece of clothing of FIG. 3 showing penetration of steam into the piece of clothing.
Figure 5:
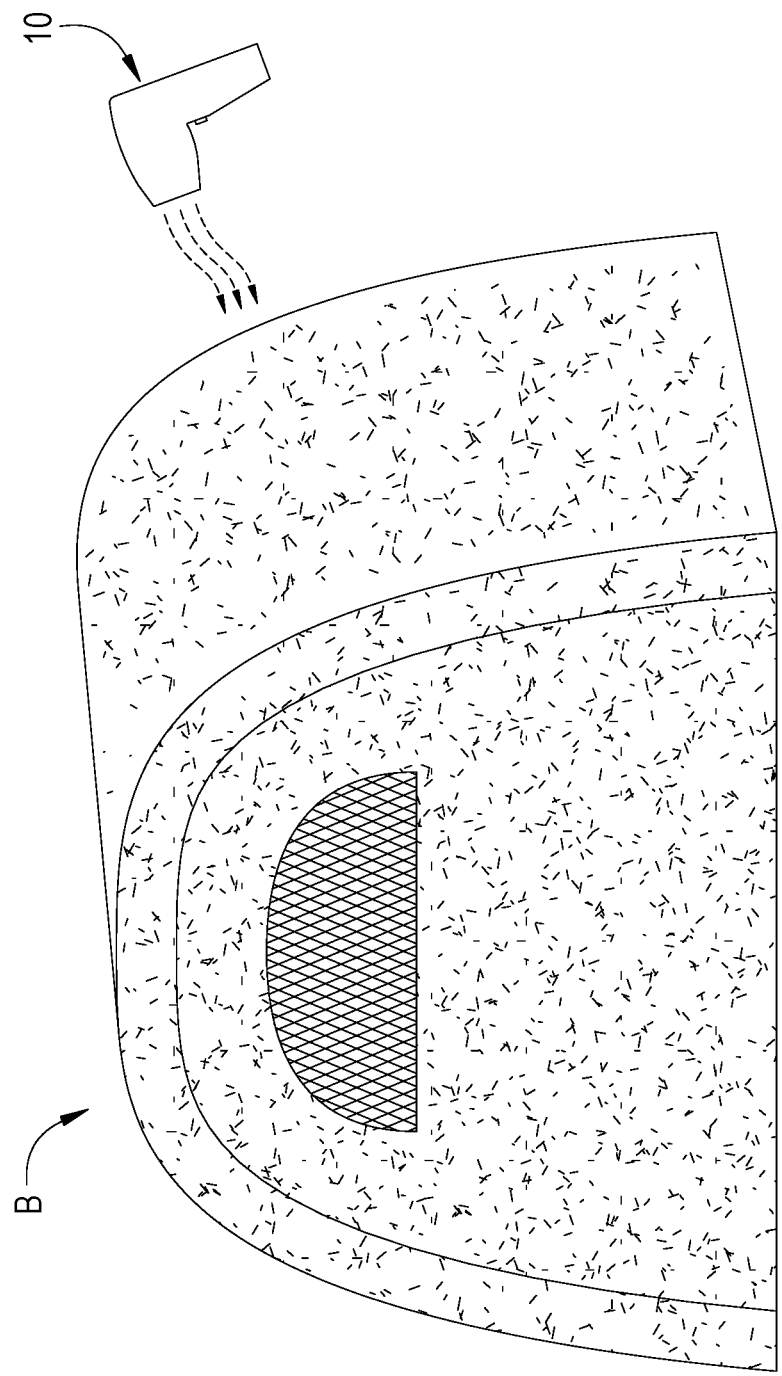
FIG. 5 is a perspective view of the steamer of FIG. 1 being used to treat a hunting blind.

The present invention is directed to a steamer and method of using same for masking or reducing undesired scents emanating from hunting gear, military gear and tactical gear. FIGS. 1 and 2 depict a cordless, hand-holdable steamer 10 and control circuit diagram therefore in accordance with the present invention. FIGS. 3 through 5 depict a piece of clothing being treated with steamer 10 in accordance with the present invention. Steamer 10 generally includes a boiler 12, a gas burner 14 for heating boiler 12, a detachable gas cartridge 16 for supplying a combustible gas to gas burner 14, and a reservoir 18 for storing a cover scent preparation or a scent reducing preparation. In use, the combustible gas is supplied from gas cartridge 16 to gas burner 14 and ignited to heat boiler 12. The cover scent preparation or the scent reducing preparation is then supplied from reservoir 18 to boiler 12 where the preparation is vaporized to produce a steam. The steam is directed out of steamer 10 and onto a piece of gear for masking or reducing undesired scents emanating from the piece of gear.

More particularly, referring to FIG. 1, there is depicted steamer 10 including a tubular housing 11 containing boiler 12, gas burner 14 arranged directly beneath boiler 12 and reservoir 18. Boiler 12 is fabricated from a material capable of conducting heat produced by burner 12 and with sufficient integrity to withstand the high temperatures created thereby. Exemplary materials include titanium, aluminum, steel and other similar metal alloys. So that boiler 12 and reservoir 18 can be cleaned, which will be needed given the residue left behind by the often oily preparations, housing 11 includes one or more removable panels situated adjacent to a side of burner 12 and a side reservoir 18, with such sides of the burner also being removable to provide access into the interior of the burner and reservoir. The panels and sides may be detachably secured to the boiler/reservoir and housing, respectively, by screws or other fasteners. Furthermore, each panel and each side, or the openings into which they are secured, include a seal for preventing liquid leakage.

A vent outlet 23 is formed through an upper portion of a front wall 25 of boiler 12 for providing an outlet through which steam may escape from boiler 12. To inhibit spilling of heated liquid out of boiler 12 through vent outlet 23, boiler 12 may include an interior wall 27 extending inwardly from a lower edge of vent outlet 23 which acts as a liquid barrier. Interior wall 27 forms a vent inlet 29 and a vent pathway 31 extending to and between vent outlet 23 and vent inlet 29 through which steam may travel.

Reservoir 18 is accessible through an opening 19 formed through a top surface of housing 11 that communicates directly with the interior of reservoir 18. Opening 19 is selectively opened and closed using a cap 21. With cap 21 removed, a desired liquid can be poured through opening 19 and into reservoir 18.

A pump 20 is arranged below reservoir 18 for pumping the liquid out of reservoir 18 and into boiler 12. This is accomplished by providing an inlet tube 22 extending to and between pump 20 and reservoir 18 thereby fluidly coupling the interior of reservoir 18 to the pump. Preferably, inlet tube 22 is coupled to a bottommost portion of an angled floor 23 of reservoir 18 to ensure efficient feeding of the liquid to the pump. To direct the liquid from pump 20 to boiler 12, an outlet tube 24 is provided which extends to and between pump 20 and boiler 12. Outlet tube 24 is arranged to deliver the liquid into boiler 12 through an opening 26 in a top wall 28 of boiler 12.

Burner 14 includes a flame shielding plate 30 for directing the heat of combustion towards a bottom wall 32 of boiler 12. An air inlet to burner 14 may be positioned in housing 11 adjacent to the burner for providing an air flow to provide for combustion of high gas flow rates. A trigger switch 33 forms a control device for initiating a flow of gas to burner 14 and operating an igniter. The igniter is an electrical means such as a piezoelectric device or a hot wire. The gas flow included a valve only opened when the supply voltage is sufficient to operate the igniter. A flame or temperature detector may be included to operate pump 20 only when burner 14 is lit. Trigger switch 33 may be a slide or other two way switch serving to open a gas valve 34 and close a pump switch 36 to drive pump 20 by a battery 38. The gas may be ignited by a separate ignition switch 40 and an igniter element 42 operatively coupled thereto. Alternatively, burner 14 may be of a catalytic or flameless kind including a coiled length of tubing which is perforated and around which is wrapped a catalyst such as asbestos fiber dipped in a salt of platinum retained by a fine wire mesh and an initiator including a wire heated by a second battery. This assembly may be encased within a heat radiating shroud.

The gas supply includes a gas cartridge 16 removably insertable into a handle 44 integral with housing 11. Alternatively, the gas supply may include a gas container provided in the handle which is charged from an external cylinder. The gas supply may be any combustible gas such as propane or butane. The handle may also include a battery, preferably a rechargeable nickel cadmium battery, a lithium-ion battery or a sealed lead-acid battery, to drive pump 20 and power igniter 42 and a flame sensor circuit, as described below.

Referring to FIG. 2, there is depicted a logic control diagram for the ignition means including a battery voltage sensor 46 to determine if sufficient power is available for correct control, followed by an ignition device 48 which turns on a gas supply 52 and effects ignition. If no gas flame or combustion is detected at 54 the ignition is re-operated but only N number of times determined by counter 56 after which the gas is shut off at 58 and a no-gas ignition indicator 60 lights. If a flame is detected the pump 62 is switched on, and the pump rate and outlet air temperature are monitored at 64 and 66, respectively. If either the pump rate or the outlet air temperature falls outside predetermined limits, the gas is shut off.

Referring to FIGS. 3 through 5, there is depicted a method of treating pieces of hunting gear A and B using steamer 10 in accordance with the present invention. According to the method, a liquid is added to 18 reservoir, as described above. The liquid is selected from commercially available cover scent and scent reducing preparations intended for use by hunters when hunting game such as deer, bear, elk, moose, coyotes, buffalo and the like. Suitable preparations are available from Ebsco Industries, Inc., Altus Brands, LLC, Buck Baits, LLC and Wildlife Research Center, Inc. The cover scent preparations may include animal urine such as fox urine, buck urine, elk urine, coyote urine, or raccoon urine or plant extracts derived from acorns, apples, pine trees and corn. Since gear A and B will be used for hunting, it is essential that the cover scent preparations do not include any constituents that may alert game animals to the presence of the hunter such as perfumes. Furthermore, it is essential that the scent reducing preparations are designed specifically to address human odors. It is contemplated that following treatment with a scent reducing preparation, steamer 10 may be used to apply a commercially available game attractant, such as deer estrous or doe urine, to the piece of hunting gear.

With reservoir 18 filled with a cover scent or scent reducing preparation, burner 14 is activated by employing ignition switch 40 to activate igniter element 42. Pump 20 and valve 34 34 are activated to supply the cover scent or scent reducing preparation to boiler 12 and gas to burner 14. Igniter element 42 ignites and combusts the gas delivered to burner 14 from cartridge 16 thereby creating heat which is used to convert the cover scent or scent reducing preparation within boiler 12 into a steam. The steam enters vent inlet 29, travels through vent pathway 31 and out of boiler 12 through vent outlet 23. The steam is then directed out of housing 11 through a nozzle 35 at temperatures ranging from 220° F. to 300° F. Steam exiting through nozzle 35 is directed upon a piece of hunting or military gear A, B thereby masking or decreasing undesired smells emanating from the piece of hunting or military gear. Hunting and military gear suitable for treatment with the method include apparel, shirts, headwear, footwear, jackets, body armor, helmets, body suits, pants, face coverings, weapons, scarves, ear coverings, gloves, underwear, socks, binoculars, seat cushions, firearms, archery bows, hunting blinds, animal calls, hunting stands, range-finders, ammunition containers, weapon cases, motor-vehicles, motor-vehicle interior fabric, Ghillie suits, parachutes, backpacks, bags, sacks, weapon holsters, hydration packs and a rappelling kits. For best results, a scent reducing preparation-based steam is applied first to the gear first, followed by application of the cover scent-based steam.

When the hunting or military gear is porous, for example, as depicted at FIG. 4, the steam penetrates the gear A thereby contacting both outer surfaces A1 and inner surfaces A2 of hunting or military gear A. Inner surfaces A2 may, in large part, include insulating materials. To ensure adequate treatment of inner surfaces A2, nozzle 35 is pressed directly against outer surfaces A2. In certain instances, the liquid binds to scent-causing chemicals located on both outer and inner surfaces, A1, A2, of the hunting or military gear A thereby neutralizing the chemicals, while the heat carried by the steam kills scent-causing organisms living on or within gear A, including over 99.9% of household germs, viruses and dust mites.

Because steamer 10 is cordless and portable, steamer 10 can be used to apply cover scent preparations and scent reducing preparations to hunting or military gear in the form of steam while in the field. For example, a hunter may apply the preparation-laden steam while wearing or transporting the gear in the field or while the hunter and gear are located in a hunting stand or blind stationed in a location were game is found. A soldier, for example, may apply the steam to gear while the soldier and gear are being transported to a site wear military operations are to take place or while the gear is being worn or carried by the soldier during a military operation. In both instances, the preparation-laden steam may be re-applied to the gear without the hunter or soldier leaving the field. As a consequence, the hunter and the soldier may treat undesired smells emanating from their gear that were acquired while the gear was in transport to the field or after leaving a house, a vehicle, an encampment or the like.

Tests

Test 1

Two identical wash clothes were sprayed with cologne and treated with a scent reducing preparation called Scent A-Way Max Odorless Odor Control, sold by Hunter Specialties. One wash cloth was sprayed with the preparation, and the other wash cloth was steamed with the preparation in accordance with the present invention. Following treatment, the smell of cologne was detectable by a human on the sprayed wash cloth, while the smell of cologne was not detectable by the human on the steamed wash cloth.

Test 2

A jacket treated by spraying with a commercially available scent reducing preparation was worn by a deer hunter in a deer stand. A mature doe appeared 284 yards downwind of the hunter and immediately caught scent of the hunter and bolted away. The following day, the hunter treated the same jacket with the same preparation but by steaming in accordance with the present invention. The hunter set up in the same hunting stand as the day before. Weather conditions were substantially identical to the day before. The mature doe appeared again approximately 284 yards downwind from the hunter, but instead of bolting, the deer walked towards the hunter coming within 5 yards of the deer stand.

As will be apparent to one skilled in the art, various modifications can be made within the scope of the aforesaid description. Such modifications being within the ability of one skilled in the art form a part of the present invention and are embraced by the claims below. For example, reservoir 18 may be located within handle 44 and formed in part by the handle wall with cartridge 16 being arranged horizontally above the reservoir inserted within handle 44 or tubular housing 11. Further, pump 20 and reservoir 18 may be excluded from steamer 10, in which instance, the liquid is added directly to boiler 12. Additionally, steamer 10 may include a fan or impeller for pushing steam out of nozzle 35. It is also contemplated that steamer 10 may be used to apply a steam composed of the scent reducing preparation to a piece of hunting or military gear, and thereafter, applying a cover scent to the gear by spraying the cover scent on the outer surfaces of the gear.

The invention claimed is:

1. A method of masking or decreasing undesired smells emanating from hunting or military gear comprising:
   providing a steamer including a body having a handle portion, a nozzle portion and a tubular housing portion extending to and between the nozzle portion and the handle portion, the tubular housing portion containing a boiler with a gas combustion device and a source of gas operatively coupled to the boiler, wherein the steamer and the body are hand-held and cordless and the source of gas is a detachable cartridge,
   supplying a liquid to the boiler, the liquid being selected from the group consisting of a cover scent preparation and a scent reducing preparation,
   using the gas combustion device to ignite and combust a gas from the source of gas thereby creating heat,
   using the heat to convert the liquid within the boiler into a steam, and
   directing the steam out of the body onto a piece of hunting or military gear thereby masking or decreasing undesired smells emanating from the piece of hunting or military gear.

2. The method of claim 1 wherein the piece of hunting or military gear is selected from the group consisting of a shirt, headwear, footwear, a jacket, body armor, a helmet, a body suit, pants, a face covering, a weapon, a scarf, ear coverings, gloves, underwear, socks, binoculars, a seat cushion, a firearm, an archery bow, a hunting blind, an animal call, a hunting stand, a range-finder, an ammunition container, a weapon case, a motor-vehicle, a motor-vehicle interior fabric, a Ghillie suit, a parachute, a backpack, a bag, a sack, a weapon holster, a hydration pack and a rappelling kit.

3. The method of claim 1 wherein the detachable cartridge contains propane or butane.

4. The method of claim 1 wherein the liquid includes urine.

5. The method of claim 1 wherein, when the hunting or military gear is porous, the steam contacts outer surfaces and inner surfaces of the hunting or military gear.

6. The method of claim 1 wherein, when the liquid is the scent reducing preparation, decreasing the undesired smells emanating from the piece of hunting or military gear to levels that are undetectable by a deer.

7. The method of claim 1 including applying the steam to the hunting or military gear in the field.

8. The method of claim 1 including using the steam to kill scent-causing bacteria located on outer surfaces and inner surfaces of the hunting or military gear.

9. The method of claim 1 including binding the liquid in the steam to scent-causing chemicals located on outer and inner surfaces of the hunting or military gear.

10. The method of claim 1 wherein the liquid is the cover scent preparation.

11. The method of claim 1 including applying steam to the piece of hunting or military gear formed from the scent reducing preparation, followed by applying steam to the piece of hunting or military gear formed from the cover scent preparation.

12. The method of claim 1 including holding the handle portion with a user's hand while directing the steam out of the body through the nozzle portion onto the piece of hunting or military gear.

13. A system for masking or decreasing undesired smells emanating from hunting or military gear comprising:
   a body having a handle portion, a nozzle portion and a housing portion extending to and between the handle portion and the nozzle portion, wherein the body is cordless and hand-holdable, a boiler disposed within the housing portion, the boiler containing a liquid selected from the group consisting of a cover scent preparation and a scent reducing preparation, a gas combustion device disposed within the housing portion and arranged in a heat exchange relationship with the boiler, a gas cartridge disposed within the body and operatively coupled to the gas combustion device, and a battery assembly disposed within the body and operatively coupled to the gas combustion device.

14. The system of claim 13 including a reservoir disposed within the body and containing the liquid and a pump disposed within the body and arranged to pump the liquid from the reservoir to the boiler.

15. The system of claim 14 including a pump switch disposed within the body and operatively coupled to the battery assembly and the pump, the pump switch being configured for selectively activating the pump.

16. The system of claim 15 wherein the pump switch is operatively coupled to the gas combustion device and the gas cartridge, the pump switch being configured for selectively supplying a gas from the gas cartridge to the gas combustion device.

17. The system of claim 13 including a gas switch disposed within the body and operatively coupled to the gas combustion device and the gas cartridge, the gas switch being configured for selectively supplying a gas from the gas cartridge to the gas combustion device.

18. The system of claim 13 including an ignition switch disposed within the body and operatively coupled to the battery assembly and the gas combustion device for activating an ignition means for initiating combustion of a gas supplied to the gas combustion device from the gas cartridge.

19. The system of claim 13 including a vent outlet formed through an upper portion of a front wall of the boiler for providing an outlet through which steam may escape from the boiler.

20. The system of claim 19 wherein the boiler includes an interior wall extending inwardly from a lower edge of the vent outlet which acts as a liquid barrier for inhibiting spilling of a heated liquid out of the boiler through the vent outlet.

21. A method of masking or decreasing undesired smells emanating from hunting or military gear comprising:

providing a steamer, adding a liquid to the steamer, the liquid being selected from the group consisting of a cover scent preparation and a scent reducing preparation, using the steamer to convert the liquid into a steam, and applying the steam to a piece of hunting or military gear thereby masking or decreasing undesired smells emanating from the piece of hunting or military gear, wherein the steamer is cordless and includes a hand-holdable housing that encloses a boiler, a gas combustion device arranged in a heat exchange relationship with the boiler, a reservoir operatively coupled to the boiler for storing the liquid and a gas source operatively coupled to the gas combustion device, the hand-holdable housing extending to and between a nozzle and a handle.

22. The method of claim 21 wherein, when the steam is produced from the scent reducing preparation, applying a cover scent fluid to the piece of hunting or military gear after application of the steam.

23. The method of claim 21 wherein, when the liquid is the scent reducing preparation and the undesired smells are human odors, decreasing the undesired smells emanating from the piece of hunting or military gear to levels that are undetectable by deer.

24. The method of claim 21 including accessing the boiler through the housing and cleaning a residue of the liquid from the boiler.

25. The method of claim 21 wherein the liquid is an oily preparation.

26. The method of claim 21 including holding the hand-holdable housing in a user's hand while applying the steam to the piece of hunting or military gear.

* * * * *